United States Patent [19]

Adam et al.

[11] 4,036,953

[45] July 19, 1977

[54] PROCESS FOR PREPARING VACCINE ADJUVANT

[75] Inventors: Arlette Adam, Palaiseau, France; Frank M. Berger, Princeton, N.J.; Louis Chedid, Paris; Edgar Lederer, Sceaux, both of France; Jean-Francois Petit, Paris, France

[73] Assignee: Agence Nationale de Valorisation de la Recherche (ANVAR), Neuilly-sur-Seine, France

[21] Appl. No.: 307,614

[22] Filed: Nov. 17, 1972

[30] Foreign Application Priority Data

Nov. 19, 1971 France .................................. 71.41610

[51] Int. Cl.² ................. A61K 39/02; C12B 1/00; C12D 13/02; C12D 13/10
[52] U.S. Cl. .................................. 424/92; 195/2; 195/4; 424/177

[58] Field of Search ............... 424/92, 177; 195/2, 195/4

[56] References Cited

U.S. PATENT DOCUMENTS 3,529,057  9/1970  Tsuchiya .......................... 424/92

OTHER PUBLICATIONS

Adam et al., Chem. Abs., vol. 77, 1972, p. 376, No. 17903j.
Chedid et al., Chem. Abs., vol. 77, 1972, p. 376, No. 17904k.
Engibarov – Chem. Abst., vol. 68 (1968), p. 85115t.

*Primary Examiner*—Albert T. Meyers
*Assistant Examiner*—Anna P. Fagelson
*Attorney, Agent, or Firm*—Weiser, Stapler & Spivak

[57] ABSTRACT

Water-soluble immunological adjuvants, extracted from mycobacteria and nocardia cells, useful for stimulating, in a host, the immune response to various kinds of antigens.

7 Claims, No Drawings

PROCESS FOR PREPARING VACCINE ADJUVANT

The present invention relates to agents effective as immunological adjuvants for stimulating, in a host, the immune response to various kinds of antigens. The invention relates more particularly to adjuvants capable of enhancing and promoting the activity of weak immunogens.

Specifically, this invention relates to adjuvant materials usable for the immunization of warm-blooded animals against bacterial and parasitic infections, as well as against various tissue antigens, both the normal and of pathological origin.

Materials having adjuvent properties have been known for some time. For instance, it is well known that materials such as mycobacterial cells and mycobacterial cell walls enhance the production of antibodies in the host and in particular, increase the host resistance to infections caused by numerous microorganisms. The known materials of this kind, such as Freund's complete adjuvant which contains whole mycobacterial cells, have been found undesirable for therapeutical usage owing to highly objectionable reactions caused thereby. Thus, they may enhance the host's sensitivity to endotoxin, cause a hypersensitivity to tuberculin and induce lung granuloma, lymphoid hyperplasia and, under certain circumstances, an experimental polyarthritis in the rat. Further, prior to the present invention, adjuvants based on mycobacterial substances, have been difficult to purify owing to their insolubility.

Water-soluble agents, extracted from mycobacteria, Nocardia cells and related microorganisms, which form the subject-matter of this invention, are free of the drawbacks inherent to previously known mycobacterial materials.

Such novel agents are free of the noxious effects inherent to the previously known preparations. These novel agents possess an adjuvant activity which is generally more potent than that of mycobacterial preparations including mycobacterial whole cells, without the objectionable effects inherent to previously known products. Furthermore, this new agent can, under suitable conditions, provide the adjuvant action upon being suspended together wih antigen in an aqueous solution, if desired in the presence of substances such as aluminum hydroxide or calcium phosphate. Finally, the water-solubility of these agents makes their purification easier to perform.

The preferred agents included among those within the scope of the invention, endowed with all the advantageous properties of mycobacterial whole cells without having the objectional secondary effects thereof, are contained in the aqueous medium in which delipidated cell walls of mycobacteria, Nocardia cells or related microorganisms have been digested in the presence of a murolytic enzyme, such as lysozyme.

Agents according to the invention are producted from cells of mycobacteria, both pathogenic and non-pathogenic, Nocardia cells and related microorganisms. As examples of mycobacteria usable as starting material in the production of adjuvants, according to the invention, there may be mentioned, inter alia, *Mycobacterium tubercolosis*, var *hominis* or *bovis* and, in particular, the Bacille Calmette Guerin (BCG); *Mycobacterium kansasii; Mycobacterium smegmatis,* or other organisms belonging to genus Mycobacterium.

The agents according to the invention can be produced by a process essentially comprising; cultivating a strain of mycobacteria, Nocardia cells or related microorganisms; recovering the cells of the cultivated strain; causing disruption thereof; taking up the disrupted cell walls, such as by differential centrifuging; separating and removing waxes, free lipids, proteins and nucleic acids; causing the delipidated material from the cell walls to be digested by means of a murolytic enzyme, such as lysozyme; eliminating the solid residue; and collecting the aqueous fraction containing said soluble agents.

In accordance with preferred embodiments of the process of the invention, the objectionable proteins are removed by means of a treatment of the material from disrupted cell walls with proteolytic enzymes, such as trypsin and chymotrypsin, whereas nucleic acids are removed by treating said material with desoxyribonuclease or DNAse, and finally free lipids and waxes are eliminated with neutral solvents such as acteone, alcohol, chloroform or mixtures of such solvents.

The agents according to the invention can be obtained in a purified form by subjecting the aqueous medium to filtration through a column of gel of polydextran or a similar material such as the gel sold under the trademark "SEPHADEX G75" or "SEPHADEX G50".

The agents of the invention seem to be formed by oligomers or portions thereof, the monomer units of said oligomers having a chemical structure similar to that of monomer units of the cell walls of microorganisms from which they have been extracted, except that the lipid moiety may be absent, or in any case, of a very small size. The monomer units of the walls include a mucopeptide combined with a glycolipid containing an arabinogalactan. A hypothetical structure of a monomer from mycobacterial cell walls (molecular weight; about 3000) has been set forth by E. Lederer in an article dealing with the chemistry of mycobacterial cell walls and published in "Pure and Applied Chemistry, 25, 1971, 135".

The agents according to the invention contain the usual animosugars and amino-acids of the cell walls.

In the following there is set forth a typical chemical analysis of a preferred agent forming the subject matter of the invention, obtained from mycobacteria of the species *Mycobacterium smegmatis;*
C = 42,84% ; H = 6,49% ; N = 3,96% ; P = 0,1% ; S = 0.

Aminosugars, consisting essentially of D-glucosamine and D-muramic acid, in equimolar proportions — 12 - 15%

Amino-acids consisting essentially of L- and D-alanine, D-glutamic acid and meso-$\chi$-$\epsilon$-diaminopimelic acid, in the ratio of 1.3:1:1 — 12 - 15%

Neutral sugars consisting essentially of D-arabinose and D-galactose, in an approximate ratio of 2:1 — 60 -70%

Lipids — less than 5%

$[2_D]$ in water: +11.3° ± 0,5°

Their sedimentation coefficient in a phosphate buffer, pH 7,0 $\mu$= 0.1, at 20° C and at a concentration of C = 4,8 mg/ml, is of the order of — $S20$ = 2,05

U.V. spectrum is characterized by a terminal absorption less than 230 nm.

i.R. spectrum shows bands at 1650 and 1520 cm$^{-1}$ amides) and at 1000–1100 cm$^{-1}$ (—OH groups).

Moreover, agents included within the scope of the invention remain stable at room temperature during at least several months and may be lyophilised without loss of activity. After lyophilisation, said agents form a flaky material, which is snow-white, readily soluble in water and providing a slightly opalescent solution. Said agents are not soluble in ether, chloroform, acetone and mixtures of ethanol-chloroform; in an ultracentrifuge, the solutions of the agent behave like a homogenous slightly polydisperse, macromolecular system.

Further features of the invention will become clear upon reading the following description concerning preferred embodiments of cultivation and extraction of materials according to the invention, said description being given merely by way of an example without limiting the scope of the invention, as described by the appended claims.

EXAMPLE 1

*Mycobacterium smegmatics* cells, a strain of which has been deposited at "American Type Culture Collection" under N° ATCC NBR 21732, are cultivated in Roux bottles on Sauton medium during about 12 days at 37° C. They are harvested by filtration on filter paper, washed with distilled water and stored at $-20°$ C until use.

A hundred grams of cells are suspended in 500ml of distilled water by cold-mixing in a Waring blender, which has been precooled, until the supension becomes homogenous. These cells are then disrupted in a precooled French press, operated in a cold room under a pressure of 420 kg/sq.cm. After a first pass, there is added 1 mg DNAse to reduce viscosity, whereafter the suspension is passed a second time through French press. In addition to the disintegration of cells by mechanical pressure, the cells may also be disrupted by sonic vibration of 30 ml of suspension during 25 minutes ($5 \times 5$ minutes) in a sonic oscillator, previously cooled and operated at 10kc/sec., as well as disrupting the cells by means of freezing-thawing, by treating them with a zeolite shaking them together with glass balls or by any conventional means usable for the disruption of microbial cells.

The resulting suspension is centrifuged three times during 15 minutes at 800 g in a refrigerated centrifuge. The pellets consisting of non-disrupted cells, are discarded. The ultimate supernatant liquor is centrifuged during an hour at 27,500 g; the pellet of cell-wall materials are returned into a suspension of 750 ml of sodium phosphate buffer (0.066 M, pH 7.8) having added thereto 125 mg trypsin, 125 mg chymotrypsin and a small portion of an antiseptic agent such as toluene, in order to preclude any bacterial contamination. The product is kept in an incubator overnight at ordinary room temperature with magnetic stirring and, thereafter, the mixture is centrifuged during an hour at 27,500 g. The pellets of cell-wall materials are washed by putting them back into suspension and centrifuging, three times with cold phosphate buffer and three times with cold distilled water.

Cell-wall material is thereafter delipidated at normal room temperature with neutral solvents. To this end, said material is put into suspension in about 30 volumes of solvent which is allowed to act during about one day with stirring. Cell-wall material is thus delipidated, three times with acetone, three times with ethanol-ether (1/1), three times with chloroform and three times with chloroform-methanol (2:1); the material is then dried with acetone. Delipidated and dried cell-wall material can be stored at room temperature until usage.

One gram of delipidated cell-wall material, obtained as aforesaid, is suspended in 250 ml of 0.1 M solution of ammonium acetate, pH 6.2; the suspension is kept overnight in the cold with a few drops of toluene. The material is filtered on a sintered-glass filter, washed with ethanol and chloroform. The washed maerial is put back in suspension in 150 ml of ammonium acetate (0.1 M, pH 6.2) having added thereto 12 mg lysozyme and a few drops of toluene; the prouct is kept overnight in an incubator of toluene; the product is kept overnight in an incubator at 37° C with stirring. After filtering on sintered glass, the residue is treated once more with lysozyme in the same conditions as before. Both filtrates are mixed, lyophilised, redissolved in water and lyophilised until removal of ammonium acetate. Yield: about 90 mg of crude water-soluble product per gram of dried delipidated cell-wall material.

The water-soluble crude product (500 mg) is filtered through a column of "SEPHADEX G50" (height; 80 cm, diameter 2.5 cm) in equilibrium with 0,1 N acetic acid. The first peak egressing from the column, well separated from the remaining products, contains the agent under consideration in a purified state (150 mg), said agent being characterized by the analytical data given above.

Filtering on a column of "SEPHADEX G75" yields a broader peak including a shoulder. Said peak appears to include two fractions of the same composition, but differing in all likelihood by their molecular weights only.

Fractions corresponding to the second peak of "SEPHADEX G50" column, which is clearly distinct from the first, contain substances of lower molecular weight, which are also included within the scope of the invention, said substances having pharmacological activities disclosed thereafter and being usable for purposes which will also appear in the following.

EXAMPLE 2

A similar preparation has been obtained from *Mycobacterium tuberculosis* var bovis, BCG strain (Institut Pasteur).

Bacilli have been cultivated 15 days on Sauton medium 37° C., washed wih distilled water and kept at $-20°$ C until use.

Cell-walls were obtained by treatment in a French press and differential centrifugation, thereafter treated with trypsin and chymotrypsin, and delipidated exactly under the same conditions as in Example 1 for *M. smegmatis*. They were then put back into suspension in ammonium acetate and digested by lysozyme exactly like in Example 1.

The obtained filtrate was lyophilised and redissolved in water several times to eliminate ammonium acetate: the thus obtained product is an adjuvant as efficient as the product obtained from *M. smegmatis*.

EXAMPLE 3

A similar formulation has been obtained from *Mycobacterium kansasii*, strain P 21 Runyon.

Bacilli were cultivated during 28 days on Sauton medium at 37° C, were killed by phenol (2%) during 48 hours, thereafter washed with distilled water and kept at $-20°$ C until use. Thereafter they were delipidated in succesion by alcohol-ether (1:1), chloroform, chloroform-methanol (2:1), dried with acetate; the deplidation with each of these solvents was repeated three times, using on each occasion a volume of solvent equal to 30 times the initial weight of bacilli.

These cells were suspended at a rate of 1 g of dried bacilli per 25 ml distilled water and subjected to ultrasonic energy, by fractions of 30 ml during 25 minutes in an apparatus of 250 watts, 10 kg/sec. The non-disrupted bacilli were removed by centrifuging (10 minutes, 500 g), put back into suspension and subjected to centrifugation (3 times). Walls were obtained by centrifuging (50 minutes, 27500 g). They were digested by trypsin and chymotrypsin, thereafter washed in the same way as in Example 1 and 2.

They were digested by lysozymes in the same conditions as in the preceding examples. The filtrate was freed by lyophilisation from ammonium acetate. The product possessed likewise adjuvant properties.

Pharmacological properties of the agents according to the invention

The agents of the invention, prepared as aforesaid, possess a powerful activity as adjuvants and are free of the serious drawbacks which were responsible for the limitations of therapeutical usage of mycobacteria and Freund's adjuvant. These highly advantageous features are evidenced by the pharmacological tests described hereunder.

In the following, the term "Substance A" refers to the agent contained in the elution fractions on "SEPHADEX" gel corresponding to the aforesaid "first peak".

The expression "Substance B" is applied to identify products resulting from lyophillisation of fractions which correspond to the "second peak" of elution in Example 1 (on "SEPHADEX G50").

A. Demonstration of the adjuvant activity of "Substances A"

When, in the tests described thereunder, Substance A has been suspended in a mineral oil, the oil was a product sold under the trademark "Bayol F", in the presence of a dispersing agent such as glycerol monooleate or the dispersing agent available under the trademark "Arlacel A". In numerous cases, properties of "Substance A" have been compared with those of whole mycobacteria or mycobacterial fractions, those of conventional Freund's complete adjuvant (FCA), those of the Freund's incomplete adjuvant (FIA), i.e., the adjuvant containing no bacteria.

In each case, Substance A was obtained from *Mycobacterium smegmatis*, except if a different source has been expressly stipulated. Further, the term Crude Substance A represents the water-soluble product obtained by digestion with lysozyme but without purification on SEPHADEX gel.

1. Adjuvant activity of Substance A, on the rate of serum antibodies with respect to ovalbumin in guinea pigs; quantitative precipitation and passive hemo-agglutination.

A soluble antigen, namely ovalbumin, was added to Substance A, to wax D (extracted from *M. tuberculosis*), to 6,6'-trehalose dimycolate known as "cord factor" and called by this name in the following (extracted from *M. kansasii*) and to Mycoside C (extracted from *M. butyricum*).

The mixture obtained in each case was added to incomplete Freund's adjuvant (FIA), then injected as an emulsion of the water-in-oil type into the foot-pad of guinea pigs. The controls comprised ovalbumin with incomplete Freund's adjuvant or complete Freund's adjuvant (FCA), the latter consisting of FIA and *M. butyricum* cells. The rates of antibodies with respect to ovalbumin were determined 21 days after injection. The induced antibody production was determined by quantitative precipitation in accordance with the method described by Gierer and Schramm (Zeit. fur Naturforsch., 1956, 116: 138), and by passive hemo-agglutination of erythrocytes coated with ovalbumin in the manner described by Stavitsky (J. Immunol., 1954, 72: 360–368). The results are summarized in Table I thereunder.

In this Table, there is shown the antibody rates after administration of the carrier alone and after administration of Substance A in an absolutely identical carrier. The Table shows that, as a rule, Substance A stimulated to a greater degree the production of antibodies than did the complete Freund's adjuvant. It is also shown, for comparison, that the said product was more active than wax D. The results indicate further the absence of adjuvant properties of both mycobacterial components previously isolated such as cord factor and mycoside C.

The numerical values appearing in the Table I correspond to the mean value of groups of 6 guinea pigs. The results are expressed in micrograms of antigen-antibody complex per ml of serum in in the case of a quantitative precipitation and as a reciprocal of serum titration in the case of hemo-agglutination.

TABLE I

Adjuvant activity of Substance A and other mycobacterial fractions on the rate of serum antibodies with respect to ovalbumin in guinea pigs. Quantitative precipitation and passive hemo-agglutination.

| Products injected and dosages per guinea-pig | Quantitative precipitation | Hemo-agglutination (reciprocal of serum titration) |
|---|---|---|
| FCA | 3532 | 4200 |
| Controls FIA | 747 | 1770 |
| FIA + "Substance A" 1μg | 2016 | 2240 |
| FIA + "Substance A" 10μg | 4715 | 2660 |
| FIA + "Substance A" 50μg | 6867 | 5440 |
| FIA + wax D of *M. tuberculosis* 200μg | 1573 | 3730 |
| FIA + "cord factor" of *M. kansasii* 50μg | 584 | 400 |
| FIA + mycoside C of *M. butyricum* 50μg | 716 | 400 |

Finally, it has been demonstrated by immunoelectrophoresis that an antigen in the presence of Substance A as well as in the presence of a complete Freund's adjuvant produces certain immuno-globulins called γ2.

2. Comparative adjuvant properties of Substance A, FIA and FCA estimated by Jerne;s technique on mice, sheep erythrocytes being used as antigens.

Substance A also increases the immunitary response to particular antigens, such as sheep erythrocytes. Substance A was administered to mice with FIA intraperitoneously, together, with $2 \times 10^7$ sheep erythrocytes in accordance with a method described by N. K. Jerne, A. A. Nordin and C. Harry in Cell-bound Antibodies, Ed. B. Ames and H. Koproviski, Wistar Institute Press, Philadelphia, (1963).

The animals used as controls comprised a first group of mice having received an injection of sheep erythrocytes exclusively in a saline solute, a second group having received injections of sheep erythrocytes exclusively in incomplete Freund's adjuvant, and a third group having received injections of sheep erythrocytes in complete Freund's adjuvant.

Three days later, the number of antibody-forming cells is determined in the spleen; Table IIA shows an increase of the number of antibody-forming cells in the spleen when sheep erythrocytes are injected together with FCA or with FIA with Substance A.

Table II A

| | Number of plate-forming cells | Increase % |
|---|---|---|
| Controls { Sheep erythrocytes + saline | 646 | — |
| Sheep erythrocytes + FIA | 703 | 9 |
| Sheep erythrocytes + FCA | 1554 | 141 |
| Sheep erythrocytes + FIA + 0.1 mg/kg | 1092 | 69 |
| Sheep erythrocytes + FIA + 1 mg/kg | 1800 | 179 |

In the following experiment adjuvant activity can be demonstrated in the absence of mineral oil and of a dispersing agent. The controls were injected with sheep red blood cells suspended only in saline or in FIA. Two other groups were treated with Substance A either in saline or suspended in FIA and the third group was treated with Substance B suspended in saline. All animals were sacrificed four days later and the number of plague forming cells was evaluated. As can be seen Table IIB both Substances A and B exerted a strong adjuvant effect even when they were mixed with sheep red blood cells in saline.

Table II B

| | Number of plate-forming cells | Increase % |
|---|---|---|
| Erythrocytes + saline solution | 3600 | |
| Erythrocytes + FCA | 3300 | |
| Erythrocytes + saline solution + "Substance A" 1mg/kg | 11500 | 330 |
| Erythrocytes + FIA + "Substance A" 1mg/kg | 15500 | 460 |
| Erythrocytes + saline solution + "Substance B" 1mg/kg | 22800 | 630 |

3. Accelerated formation of antibodies against influenza virus following administration of Substance A to mice 10 g Swiss mice were injected subcutaneously with UV inactivated Pr 8 influenza virus in water, FIA or FIA containing various doses of Substance A; Groups of 5 mice were bled from the retro-orbital virus at weekly intervals starting 14 days later. Hemaggbutination tetrations were carried out on the pooled sera (HIRST G.K., Science (1941) 94, p. 22) and the geometric mean of four titration was calculated as is evidenced in Table III. Substance A stimulated antibody response at doses of 50 and 5 μg per mouse. At 42 days there was a twelvefold increases in antibody levels in the 50 μg group.

Table III

| Adjuvant | Antibody titrations | | | | |
|---|---|---|---|---|---|
| | 14 | 21 | 28 | 35 | 42 |
| Controls: saline solution + virus | 4.0 | 8.0 | 13.4 | 16.0 | 16.0 |
| Controls: FIA + virus | 11.3 | 19.0 | 32.0 | 45.0 | 64.0 |
| FIA + virus + "Substance A" 50μg/mouse | 32.0 | 64.0 | 215.0 | 305.0 | 722.0 |
| FIA + virus + "Substance A" 5μg/mouse | 11.3 | 32.0 | 90.0 | 108 | 152 |
| FIA + virus + "Substance A" 0.5μg/mouse | 4.0 | 8.0 | 22.0 | 45.0 | 108.0 |

4. Increased formation of antibodies against virus Columbia SK

The properties of Substance A are also shown for other viruses such as Columbia SK. A vaccine was prepared and killed by exposing a preparation of high titration Columbia SK to U.V. light. In this test, the titration expressed as inefecting power, was lowered from 8.32 to 1.85 log ufp/ml. This inoculum was injected to mice either alone or together with FIA including or not including Substance A. As shown in Table IV, Substance A administered with the vaccine strongly stimulated the immunitary response 14 days later.

Table IV

| Treatment | Antibody titration after 14 days |
|---|---|
| Vaccine alone | 2 |
| Vaccine + FIA | 37 |
| Vaccine + FIA + "Substance A" 100 μg/mouse | 181 |

5. Protective action of Substance A on survival of mice infected with virus Columbia SK In this experiment, the virus was given in concentrations which caused the death of most of the untreated animals. Substance A, with FIA and a homologuous viral vaccine administered three weeks before the inoculation of virus protected from death a substantial proportion of animals and appreciably lengthened the time of their survival. Substance A appeared to be more effecient than Freund's complete adjuvant.

Table V

| | Mortality | | |
|---|---|---|---|
| Adjuvant | Number of animals dead | Number of animals treated | Mean time of survival (days) |
| Nil | 26 | 29 | 5.59 |
| FIA | 26 | 28 | 6.25 |
| FCA | 22 | 26 | 6.15 |
| FIA + "Substance A" 100μg/mouse | 20 | 29 | 7.28 |

B. Demonstration of inocuity of Substance A

The following tests demonstrate the lack of toxicity of Substance A.

1. Hyperreactivity to endotoxins

It is well established that mycobacteria increase the susceptibility to the lethal effect of endotoxins (Suter, E, and Coll. 1958, Proc. Soc. Exp. Biol. Med, 1958, 99, 167; Halpern, B.N. and Coll., C.R. Soc. Biol. Paris, 1958, 152, 899).

It has been admitted that this activity is related to the cord factor (E. Suter et Coll., Proc. Soc. Exp. Biol. Med. 1958, 99, 1967).

Mice were sensitized 14 days before their being challenged with endotoxin, by injections, either with BCG (Bacille Calmette Guerin) killed by phenol and in the form of whole cells or delipidated cells, or by whole cells of *Mycobacterium smegmatis* killed by phenol. Two different samples either crude Substance A (not fractured by SEPHADEX) or of purified Substance A have also been tested. In each case, mice received intravenous injections at doses of 300 μg of the product under assay in suspension in saline or in Bayol.

It should be noted that Bayol must be used at a final concentration of 50% to provide an adjuvant action, as in the case of complete Freund's adjuvant. However, in the experiments under consideration relating to the hyperreactivity towards an endotoxin (Table VI), the injections comprised in all cases 0.2 ml of mycobacterial preparations suspended in a medium containing 10% of Bayol.

Two weeks later, all mice received an intravenous injection of an endotoxin preparation extracted from *Salmonella enteriditis*, strain Danysz. The $LD_{50}$ of this preparation suspended in saline and injected to normal controls corresponds to 240 µg.

As may be seen from Table VI:

a. $LD_{50}$ of endotoxin was multiplied by 200 when whole BCG has been administered to misc, while administration of delipidated BCG was without effect when the cells were suspended in a saline solute. However, when delipidated BCG was suspended in Bayol, the sensitizing effect of this mycobacterial preparation was recovered. Injection of Bayol alone to controls did not sensitize mice to endotoxin.

b. Administration of whole heat-killed *M. smegmatis* (strain from which Substance A has been prepared) sensitized to a much smaller degree than BCG to endotoxins. Nevertheless the suspension of *M. smegmatis* in Bayol sensitized strongly the mice to endotoxin.

c. Crude Substance A did not sensitize to endotoxin when suspended in saline or even in Bayol.

Table VI shows the amounts of endotoxin injected per mouse.

after injection. This latter activity can also be caused by cord factor suspended in paraffin oil (Bekierkunst and al., J. Bacteriol., 1969, 100, 95-102). In the following tests, mice received either cells (killed with phenol) of BCG or *M. smegmatis*, or Substance A. BCG was suspended in saline, whereas *M. smegmatis* and Substance A were suspended either in saline, or in "Bayol" at a concentration of 10%. All injections were intravenous at a volume of 0.2 ml and the animals were sacrificed 14 days later.

As shown in Table VII, 300 µg of BCG suspended in saline caused substantial hepatomegaly and splenomegaly. Suspended in saline, 300 µg of *M. smegmatis* led to an increase of the weight of the lung and the spleen. These effects were considerably stronger when 300 µg of *M. smegmatis* were suspended in Bayol and, in this case, the liver was also hypertrophied. On the contrary, after injection of Substance A suspended in a saline solution or even in Bayol, no detectable augmentation of the weight of various organs, compared to the controls, was noted.

3. Sensitivity to tuberculin

Guinea pigs were sensitized by subcutaneous injections of whole cells killed with phenol of BCG (0.2 or 2 mg), of *M. smegmatis* (2 mg) or *M. kansassii* (2 mg). A few guinea pigs were treated either with crude Sub-

Table VI

| | Hyperreactivity to an endotoxin | | | | | | |
|---|---|---|---|---|---|---|---|
| | Endotoxin (µg par souris) | | | | | | |
| | 0.15 | 0.5 | 1.5 | 5 | 15 | 50 | $DL_{50}$ |
| Controls (Bayol) | — | — | 0/8+ | 0/8 | 0/15 | 0/15 | >50 |
| BCG* (saline solute) | 0/18 | 22/42 | 34/58 | 48/58 | 46/56 | 45/45 | 1.3 |
| BCG delipidated* (saline solute) | — | — | 0/8 | 0/8 | 1/33 | 4/33 | >50 |
| BCG delipidated* (Bayol) | — | — | 6/7 | 7/7 | 7/7 | 7/7 | <1.5 |
| *M. smegmatis** (saline solute) | — | — | 2/25 | 3/24 | 4/26 | 11/25 | 37.9 |
| *M. smegmatis** (Bayol) | — | 8/16 | 11/16 | 13/16 | 12/16 | 8/8 | 1.1 |
| "Substance A" crude* (saline solute) | — | — | 0/8 | 0/18 | 0/18 | 1/35 | >50 |
| "Substance A" crude* (Bayol) | — | — | 1/6 | 0/13 | 0/14 | 0/14 | >50 |
| "Substance A" * (Bayol) | — | — | — | — | — | 1/10 | >50 |

+ Dead / total
*In each case, the dosage is 300 µg per mouse.

2. Lung granuloma and lymphoid hyperplasia

It is well established that upon being injected intravenously, mycobacteria cause hypertrophy of the liver and of the spleen as well as lung granuloma measurable by an increase of the weight of said organs, 3 to 14 days stance A (0.2 or 2 mg) or with two different preparations of purified Substance A (0.2 mg). In all cases, mycobacterial substances were suspended in incomplete Freund's adjuvant (final concentration of Bayol = 50%).

Table VII

| Absence of hypertrophy of lungs, liver or spleen after administration of "Substance A" | | | | | | | | | |
|---|---|---|---|---|---|---|---|---|---|
| | | Number of mice | Weight of liver (mg) | | | Weight of spleen (mg) | | Weight of lungs (mg) | |
| Controls | saline solute | 8 | 1073 | ± | 186 | 123 | ± 38.8 | 153 | ± 13.7 |
| BCG 100 µg | | 7 | 1275 | ± | 311 | 170 | ± 71.3 | 170 | ± 14.9 |
| BCG 300 µg | | 7 | 1767** | ± | 269 | 338** | ± 107.3 | 170 | ± 22.5 |
| *M. smegmatis* 100 µg | | 7 | 1119 | ± | 160 | 139 | ± 28 | 163 | ± 19.2 |
| *M. smegmatis* 300 µg | | 6 | 1215 | ± | 282 | 194* | ± 63.7 | 182* | ± 25.8 |
| "Substance A" 100 µg | | 7 | 1115 | ± | 162 | 153 | ± 35.5 | 158 | ± 9.9 |
| "Substance A" 300 µg | | 8 | 1065 | ± | 117 | 138 | ± 35.8 | 161 | ± 14.5 |
| Controls | "Bayol" | 7 | 1029 | ± | 159 | 118 | ± 18.3 | 160 | ± 23.6 |
| *M. smegmatis* 100 µg | | 8 | 1092 | ± | 202 | 156 | ± 51.8 | 196 | ± 38.1 |
| *M. smegmatis* 300 µg | | 8 | 1761** | ± | 382 | 321** | ± 89.3 | 225** | ± 31 |
| "Substance A" 100 µg | | 10 | 1050 | ± | 269 | 142 | ± 64.6 | 171 | ± 40.2 |
| "Substance A" 300 µg | | 9 | 1128 | ± | 238 | 157 | ± 52.5 | 156 | ± 21.8 |

Mice used in this test are hybrids $F_1$ (CBA/T6/T6 × AKR). Dosages are expressed in micrograms per mouse.
*P 0.05
**P 0.01

Table VIII

Lack of sensitivity to tuberculin of "Substance A"

|  | Reaction at 100 i.u. of tuberculin | | | Reaction at 300 i.u. of tuberculin | | |
|---|---|---|---|---|---|---|
|  | Diameter | Mean Diam. | Intensity | Diameter | Mean Diam. | Intensity |
| FIA + BCG 0,2 mg | 2-2-3-1-3-3 | 2.3 | + | 2-2-5-4-4-4 | 3.5 | ++ |
| FIA + BCG 2 mg | 8-6-7-4-6-3-4-3-5-6-5 | 5.2 | +++ | 10-8-12-9-10-8 | 9.5 | ++++ |
| FIA + M. smegmatis 2 mg |  |  |  | 7 | 7 | +++ |
| FIA + M. kansasii 2 mg | 0-2-2-3-1-3-2-2-2-7-6-6 | 3 | ++ | 8-7-8-9-6 | 7.6 | +++ |
| FIA + "Substance A" crude 0,2 mg | 0-0-1 | 0.3 | − | 0-1-2 | 1 | + |
| FIA + "Substance A" crude 2 mg | 0-0-2-0 | 0.25 | − | 2-0 | 1 | + |
| + "Substance A" 0.2 mg | 0-0-0-0-0-0-0-0-0 | 0 |  | 0-0-0-0-0-0-0-0-0 | 0 | − |

The sensitivity of these animals was measured 21 days later by intradermic injection of 100 I.U. or 300 I.U. tuberculin. Glycerol was also injected, as a control substance.

As seen in Table VIII, necrosis and strong cutaneous reactions were caused by tuberculin when guinea pigs had been sensitized by FIA containing BCG or M. smegmatis or M. kansassi, but these phenomena did not take place when the animals had been sensitized with Substance A added to Freund's incomplete adjuvant.

4. Pyrogenic activity

It is well known that numerous bacteria contain fever causing substances. The usual method for estimating the pyrogenic activity consists in injecting substances to rabbits and measuring the resulting rise of temperature.

Under these conditions, 0.01 μg/kg caused a fever response and with 0.05 μg/kg a substantial rise of temperature. BCG (whole cells) killed by phenol and Substance A were injected to rabbits at dosages of 5 to 100 μg/kg and the rise of temperature was determined at different times after administration. It is noted that 100 μg of BCG induced the same response than 0.05 μg of endotoxin and 100 μg Substance A induced a rise in temperature which was only of the same order of magnitude was that obtained with 5 μg/kg of BCG.

These results are summarized in Table IX.

Table IX

| Preparation | Surface of area under temperature curve (cm$^2$) | Maximum rise of temperature (° C) |
|---|---|---|
| Endotoxine (Difco LPS) 0.05 μg | 17.6 ± 1.9 | 1.33 ± 0.11 |
| BCG 5 μg | 6.3 ± 1.7 | 0.78 ± 0.22 |
| BCG 100 μg | 17.0 ± 4.1 | 1.33 ± 0.28 |
| "Substance A" 5 μg | 2.8 ± 0.6 | 0.39 ± 0.11 |
| "Substance A" 100 μg | 9.6 ± 5.1 | 0.78 ± 0.39 |

5. Experimental polyarthritis of the rat

A mixture of paraffin oil and killed mycobacteria was used to induce experimental polyarthritis of the rat (Pearson and Wood, Arthr. and Rheum, 1959; 2: 440-459). This phenomenom is considered as an autoimmune reaction. Thus when complete Freund's adjuvant is injected in the foot pad of rats, there may be seen an articular oedema which is the most pronounced in the leg having received an injection with Freund's adjuvant but which is also visible in all the other articultions.

Modifications at the articular level which may be measured by the volume or the weight of the legs are very substantial after 7 days and reach their maximum value 14 days after injection. The arthritis induced in this way is accompanied by variations of albumin/globulin ratios in the blood.

In the following test (Table X), groups of 10 ratios in the blood.

In the following test (Table XI), group of 10 rats received FIA containing either cells of M. tuberculosis (5 or 2 mg/ml) or Substance A (2 mg/ml). Further, two groups of controls received either an injection of saline solute alone or an injection of this solute containing Substance A (2 mg/ml). All injections were effected in one of the hind legs at a volume of 0.1 ml. The rats were killed 17 days later.

It is noted that the mixture of FIA and mycobacteria (even at a dosage of 2 mg/ml) increased considerably the volume of both hind legs, reduced the gain of the body weight and reversed the ratio of albumin to globulin. On the contrary, animals treated with Substance A in saline behaved like normal controls and, even when Subtance A had been administered together with FIA, the albumin/globulin ratio and the body weight were not effected whereas the volume of both hind legs increased only slightly (Table X). This slight increase was moreover due to the presence of FIA alone, as will be shown by the following experiment.

In this experiment (Table XI), groups of ten rats received FIA in admixture either with mycobacteria (5 mg/ml) or with Substance A (5 mg/ml and 0.5 mg/ml). Moreover, two groups of control animals received an injection only of saline or of FIA. The injections were carried out under the same conditions as previously, but rats were killed 14 days later and arthritis was estimated by an increase of the weight of legs in relation to that of control animals.

It is noted that Subtance A, even at a dosage of 5 mg/ml, induced only a slight inflammation of the same order as that observed in the control animals having received only FIA and much smaller than in animals having received FIA and 5 mg of mycobacteria. Likewise, Substance A did not decrease the gain of body weight as in the case with a mixture of mycobacteria and FIA (Table XI).

Table X

|  | Hind legs | | Increase | |
|---|---|---|---|---|
|  | volume (ml) | Increase (%) | of body weight (%) | Albumin/globulin ratio |
| Saline solute (controls) | 4.85 ± 0.064 | — | 100 | 2.18 ± 0.165 |
| FIA + Mycobacteria 5 mg/ml | 8.31 ± 0.471 | 100 | 42 | 0.70 ± 0.094 |
| FIA + Mycobacteria 2 mg/ml | 7.34 ± 0.315 | 72 | 71 | 0.68 ± 0.091 |
| Saline solute + "Substance A" 2 mg/ml | 4.71 ± 0.094 | 0 | 105 | 1.97 ± 0.165 |

Table X-continued

|  | Hind legs | | Increase | |
|---|---|---|---|---|
|  | volume (ml) | Increase (%) | of body weight (%) | Albumin/globulin ratio |
| FIA + "Substance A" 2 mg/ml | 5.50 ± 0.136 | 19 | 104 | 1.73 ± 0.071 |

Table XI

|  | Hind legs | | Injected leg | | Increase of body weight (%) |
|---|---|---|---|---|---|
|  | Weight (g) | Increase (%) | Weight (g) | Increase (%) |  |
| Saline solute (controls) | 3.47 ± 0.121 | — | 1.74 ± 0.073 | — | 100 |
| FIA (controls) | 4.04 ± 0.235 | 27.08 | 2.31 ± 0.141 | 24.7 | 84.5 |
| FIA + Mycobacteria 5 mg/ml | 5.62 ± 0.146 | 100 | 4.05 ± 0.143 | 100 | 32.5 |
| FIA + "Substance A" 5 mg/ml | 4.10 ± 0.170 | 30.7 | 2.34 ± 0.123 | 26 | 89 |
| FIA + "Substance A" 0.5 mg/ml | 4.02 ± 0.242 | 27.1 | 2.31 ± 0.126 | 24.7 | 95 |

C. Comparison between adjuvant activity of preparations extracted from three different mycobacterial strains All the foregoing biological results were obtained with Subtance A extracted from *M. smegmatis*. This water-soluble fraction has also been prepared from *M. kansasii* or from BCG (see examples of preparations 2 and 3). The thus obtained preparations had also an adjuvant activity. This activity has been established by measuring the serum antibodies in a guinea pig immunized by ovalbumin; in the following test (Table XII), this antigen was mixed with crude Substance A (before fractioning on SEPHADEX) extracted from BCG or *M. kansasii*, the mixture being suspended in Freund's incomplete adjuvant. As previously, ovalbumin was administered to control aniamals either with FIA or with FCA. The conditions of the test are the same as in Example 1 (described in connection with Table 1).

Numerical values in Table XII represent the mean value calculated on groups of six guinea pigs. Results are expressed as micrograms of antigen-antibody complex per ml of serum in the case of quantitative precipitation and as a reciprocal of serum titration in the case of hemo-agglutination.

It can be seen that Substance A, whether extracted from *M. smegmatis, BCG, or M. kansasii*, stimulated the production of antibodies in the same way as Freund's complete adjuvant.

Table XII

|  | Quantitative precipitation | Hemo-agglutination (reciprocal of serum titration) |
|---|---|---|
| FCA | 2060 | 4640 |
| FIA (controls) | 100 | 440 |
| FIA + crude "Substance A" BCG* | 3940 | 5600 |
| FIA + crude "Substance A" M. kansasii* | 3950 | 4640 |

*200 µg per guinea pig

D. Adjuvant activity of substances collected in the fractions corresponding to the second peak of elution of agents extracted from *M. smegmatis*

The product (Substance B) made by lyophillisation of fractions corresponding to the second peak of elution of Example 1 possesses likewise, as already said, an adjuvant action. This action has been evidenced by measuring serum antibodies produced by ovalbumin administered in admixture with Subtance B suspended in FIA. The effects of Subtance B were compared to those of controls having received FIA or FCA.

Table XIII

| Products injected and | Quantitative precipitation |
|---|---|
| Controls FIA | 650 |
| Controls FCA | 4030 |
| FIA + "Substance B": 200 µg | 8200 |
| Controls FIA | 750 |
| Controls FCA | 3530 |
| FIA + "Substance B" repurified by a further filtration on SEPHADEX G50: 50 µg | 4990 |

According to the invention there are thus provided adjuvants having a considerable activity while free of objectionable side effects which have limited up to now the use of mycobacteria for preventing or treating diseases in animals and in men. Materials included within the scope of the present invention are used to increase the efficiency of vaccine whether of bacterial or viral origin, especially if they are weak immunogens. They can be used, in particular, to enhance immunization of the hosts (humans or animals) with respect to bacterial diseases, anitgens such as, protozoan antigens, etc. They may also be used efficiently for the production of serums. Substance A can be suspended in the incomplete Freund's adjuvant or in a carrier comprising, for instance, 8.5 parts hexadecane, 1.5 parts of Arlacel or glycerol monooleate and 10 parts of saline solution. The same is true for Substance B.

Finally, it is particularly worth to note that Substance A, under suitable conditions of use, may reveal its adjuvant activity even upon being added to antigen in an aqeuous solution. The same is true for Substance B.

The administration can be carried out in the form of typical compositions of the vaccine type, by intramuscular injection, intradermic injection, or subcutaneous injection, as well as scarification.

It is to be understood that the foregoing description has been given merely by way of an example, without any intent to limitation, the scope of the invention being defind by the appended claims.

What is claimed is:

1. In a process for preparing a water-soluble immunological non-specific adjuvant for enhancing the effect of vaccine, the improvement which comprises
    treating with a murolytic enzyme, in an aqueous solution, a suspension of Mycobacteria or Nocardia cells walls, said cell walls being substantially free of waxes, free lipids, free proteins and of nucleic acids,
    separating the solid residue including cell walls residue from the digested residue and, recovering the aqueous portion containing water-soluble immunological adjuvant, the adjuvant having reduced sensitizing action to tuberculin.

2. The process of claim 1 wherein the murolytic enzyme is lysozyme.

3. The process of claim 2 which comprises the additional step of lyophilizing the aqueous fraction containing the immunological adjuvant and collecting a water-soluble product which is insoluble in ether, chloroform, acetone and a mixture of ethanol and chloroform.

4. The process of claim 3 which comprises the additional step of making a aqueous solution of the dry lyophilized extract.

5. The process of claim 4 which comprises the additional step of filtering the aqueous solution of the immunological adjuvant on a molecular sieve and recovering the filtrate containing the more purified aqueous solution of the immunological adjuvant.

6. The process of claim 5 wherein the molecular sieve is of a polydextran gel.

7. The process of claim 6 which comprises taking off several fractions from the column and collecting either the first or second fraction of the aqueous filtrate, said fractions containing the more purified immunological adjuvant.

* * * * *